United States Patent [19]

Kim et al.

[11] Patent Number: 5,952,227
[45] Date of Patent: Sep. 14, 1999

[54] HUMAN EMBRYONIC LUNG FIBROBLAST DIPLOID CELL STRAIN SUITABLE FOR THE PRODUCTION OF VIRUS AND PROCESS FOR THE PRODUCTION OF VARICELLA ZOSTER VIRUS USING SAME

[75] Inventors: Jeong Min Kim; Bock Ryeon Park; Joo Hong Park, all of Daejeon, Rep. of Korea

[73] Assignee: LG Chemical Ltd, Rep. of Korea

[21] Appl. No.: 08/945,136

[22] PCT Filed: Feb. 15, 1997

[86] PCT No.: PCT/KR97/00028

§ 371 Date: Oct. 14, 1997

§ 102(e) Date: Oct. 14, 1997

[87] PCT Pub. No.: WO97/30147

PCT Pub. Date: Aug. 21, 1997

[30] Foreign Application Priority Data

Feb. 16, 1996 [KR] Rep. of Korea ............... 96 3876

[51] Int. Cl.[6] ................ C12N 5/08; C12N 7/00; C12N 7/02
[52] U.S. Cl. .............. 435/366; 435/235.1; 435/239
[58] Field of Search .................. 435/239, 235.1, 435/366

[56] References Cited

U.S. PATENT DOCUMENTS 3,985,615  10/1976  Kubo ............................ 195/1.3
4,338,335  7/1982  McAleer et al. ................ 424/361
5,310,668  5/1994  Ellis et al. ...................... 435/172.3
5,756,281  5/1998  Martin ............................ 435/5

FOREIGN PATENT DOCUMENTS 573 107  12/1993  European Pat. Off. .

OTHER PUBLICATIONS

Jacobs et al., "Characterization of a human diploid cell designated MCR–5", Nature, 1970, vol. 227, pp. 168–170.

Hayflick et al., "The Serial cultivation of human diploid cell strains", Experimental Cell Research, 1961, vol. 25, pp. 585–621.

*Primary Examiner*—Sandra E. Saucier
*Assistant Examiner*—Afremova Vera
*Attorney, Agent, or Firm*—Anderson Kill & Olick

[57] ABSTRACT

A human embryonic lung fibroblast diploid cell strain LBHEL(KCTC 0127BP) is highly susceptible to varicella zoster virus(VZV). A cell-free varicella zoster virus (VZV) is produced by (a) culturing the human embryonic lung fibroblast diploid cell strain LBHEL(KCTC 0127BP) of claim 1 in a culture vessel to give cultured LBHEL cells; (b) infecting the cultured LBHEL cells with VZV to give VZV-infected cells; (c) culturing and harvesting the VZV-infected cells; (d) disrupting the harvested cells to obtain a cell homogenate; and (e) centrifuging the cell homogenate to obtain a supernatant containing the cell-free VZV.

11 Claims, 4 Drawing Sheets

HUMAN EMBRYONIC LUNG FIBROBLAST
DIPLOID CELL STRAIN SUITABLE FOR
THE PRODUCTION OF VIRUS AND
PROCESS FOR THE PRODUCTION OF
VARICELLA ZOSTER VIRUS USING SAME

FIELD OF THE INVENTION

The present invention relates to a novel human embryonic lung fibroblast diploid cell strain suitable for producing a virus and a process for the preparation of varicella zoster virus using same as a host cell.

DESCRIPTION OF THE PRIOR ART

Viruses cause various diseases such as measles, rubella, mumps, chickenpox, epidemic hemorrhagic fever, Japanese B encephalitis, infantile poliomyelitis, hepatitis A, hepatitis B, hepatitis C and variola. These viral diseases can be prevented by inoculation with vaccines prepared from inactivated or attenuated pathogenic viruses.

Generally, embryonated chicken eggs, infant rat brain cells and diploid cells of mammals have been used as host cells for producing such virus vaccines. Although embryonated chicken eggs or infant rat brain cells may be used as host cells to reduce the production cost, they are disadvantageous due to their low susceptibility to viruses, complicated purification processes and side effects brought about by the presence of foreign protein contaminants. In contrast, the use of normal diploid cells originating from human can reduce the side effects caused by foreign proteins, and thus, they are more preferred in preparing virus vaccines.

Representative human diploid cells include MRC-5 cell strain(ATCC, CCL 171), WI-38 cell strain(ATCC, CCL 75) and HEL 299 cell strain(ATCC CCL 137): Specifically, MRC-5 cell strain originated from the lung tissue of a 14-week old male embryo[*Proc. Symp. Human Diploid Cells*, Yugoslavia. Acad. SCI. Arts. Zagreb., pp43–45(1970); and *Nature*(London), 227, pp168–170(1970)]; WI-38 derived from the lung tissue of a 3 month-old female embryo[*Exp. Cell Res.*, 25, p585(1961); and *Am. J. Hyg.*, 75, p240(1962)]; and HEL 299 cell strain obtained from the lung tissue of a male embryo[W. D. Peterson, Jr. et al., *Proc. Soc. Exp. Biol. Med.*, 128, p772(1968)].

Chickenpox is a highly contagious disease that afflicts children, aged people and patients having reduced immunity due to the infection by varicella zoster virus(VZV). It has been reported that VZV can be cultured in various cells such as a human amnion cell, human thyroid cell, human lung cell, human cervix hela cell and monkey kidney cell[see E. V. Meurisse et al., *J. Microbiol.*, 2, 317(1969)]. Further, U.S. Pat. No. 3,985,615 discloses the production of VZV vaccine by multiple attenuation of Oka virus in a guinea pig primary embryonic tissue cell(GPEC); U.S. Pat. No. 4,000,256 describes the production of VZV vaccine by subculturing 10 to 80 times the human embryonic fibroblast WI-38 cell strain containing VZV virus; U.S. Pat. No. 4,000,317 reported the production of temperature-sensitive mutant VZV in WI-38 cell strain; and U.S. Pat. No. 5,360,736 discloses an improved method for the production of VZV vaccine in MRC-5 cell strain.

However, the yield of VZV is very low in GPEC cells. Further, WI-38 and MRC-5 cell strains have high passage numbers, thereby reducing their capability to produce VZV. Therefore, the above method cannot be applied in a large scale production of VZV vaccine. Further, VZV tends to become inactivated in a cell-free environment owing to its cell-dependent properties.

SUMMARY OF THE INVENTION

Accordingly, it is an object of the present invention to provide a novel human diploid cell strain having a high susceptibility to various viruses, especially to VZV and providing a high yield of VZV.

It is another object of the present invention to provide an improved process for producing VZV.

In accordance with one aspect of the present invention, there is provided a fibroblast diploid cell strain LBHEL (KCTC 0127BP) derived from a human embryonic lung cell.

In accordance with another aspect of the present invention, there is also provided a process for producing a cell-free varicella zoster virus (VZV) comprising the steps of:

(a) culturing a human embryonic lung fibroblast diploid cell strain LBHEL(KCTC 0127BP) in a culture vessel to give cultured LBHEL cells;

(b) infecting the cultured LBHEL cells with VZV to give VZV-infected cells;

(c) culturing and harvesting the VZV-infected cells;

(d) disrupting the harvested cells to obtain a cell homogenate; and (e) centrifuging the cell homogenate to obtain a supernatant containing the cell-free VZV.

BRIEF DESCRIPTION OF THE DRAWINGS

The above and other objects and features of the present invention will become apparent from the following description thereof, when taken in conjunction with the accompanying drawings wherein:

FIGS. 1—1 and 1–2 show the karyotype of the LBHEL cell strain of the present invention;

DETAILED DESCRIPTION OF THE INVENTION

As used herein, the term "cell-free virus" means a virus which is not associated with its host cell.

The novel LBHEL cell strain of the present invention derived from a human embryonic lung fibroblast diploid cell may be produced as follows:

First, a small portion of human embryonic lung tissue is taken from a 20-week old female embryo having a karyotype of FIGS. 1—1 and 1–2. The tissue is cut into small pieces and washed with a phosphate buffer(pH 7.1 to 7.3). The tissue is then cultured in a phosphate buffer containing collagenase and dispase ("enzyme solution") at a temperature ranging from 36 to 37° C. under an atmosphere of 5% $CO_2$ for 5 to 10 minutes. The resulting culture is centrifuged at 30 to 50×g and the precipitated lung tissue is cultured in the above enzyme solution at a temperature ranging from 36 to 37° C. for 20 to 40 minutes. The supernatant of the resulting culture is then neutralized with 5%(v/v) fetal bovine serum(FBS). This enzyme treatment is repeated 3 or 4 times until only connective tissues remain.

Then, the combined tissue extract is allowed to stand at a temperature ranging from 4 to 5° C. for about 1 hours to precipitate out the cell aggregates, and the resulting supernatant containing single cells is separated and centrifuged at 800 to 100 rpm for 1 to 2 minutes. The precipitated cells are collected, dispersed in a Dulbecco's modified eagle's medium (DME medium) containing 5 to 10%(v/v) FBS to a concentration ranging from $5–10 \times 10^6$ cells/ml, and then cultured in a T80 flask at 36 to 37° C. until the surface of the culture vessel becomes covered with cells. After a trypsin treatment, the cultured cells are subjected to serial subcultures.

The LBHEL cell strain of the present invention produced as above was deposited on Nov. 9, 1994 with the Korean Collection for Type Cultures(KCTC) (Address: GERI, KIST, P.O. Box 115, Yusong, Taejon, 305–600, Republic of Korea) under the accession number, KCTC 0127BP, in accordance with the terms of Budapest Treaty on the International Recognition of the Deposit of Microorganism for the Purpose of Patent Procedure. The current depository collection name and address: Korea Research Institute of Bioscience and Biotechnology (KRIBB) 52, Oun-Dong, Yusong-Ku, Taejon 305–333, Republic of Korea.

The LBHEL cell strain of the present invention is confirmed to be a normal diploid cell strain by a chromosome abnormality test and it does not cause tumor in animal tests. Further, it grows much faster than conventional cell strains such as MRC-5 and HEL299 and has increased susceptibility to various viruses. Moreover, it maintains the same growth rate even after 30 subculture generations.

The novel LBHEL cell strain of the present invention has the following characteristics:
(1) Cell Growth Rate In comparison with the MRC-5 standard cell strain, the LBHEL cell strain grows faster by a factor of about 2 and the number of cells produced therefrom in a fixed surface area is greater than that of MRC-5 by a factor of 1.7 or more.
(2) Plaque Identification When the LBHEL cell strain of the present invention is used as a host cell to measure the titer of virus, the plaque formed can be readily identified and its reproducibility is better than that of MRC-5.
(3) FBS Content The conventional human diploid normal cell strains including MRC-5, WI-38 and HEL299 are generally cultured in a medium containing 10%(v/v) FBS, whereas the LBHEL cell strain of the present invention grows well in a medium which has an FBS content of only 5%. Since FBS is expensive, the LBHEL cell strain offers a considerable advantage in reducing the production cost.
(4) Susceptibility to VZV As shown in Table I, the LBHEL cell strain of the present invention has much higher susceptibility to VZV than the conventional human diploid normal cell strains which include MRC-5, HEL299 and Lul8. This suggests that VZV grows more easily in the LBHEL cell strain of the present invention than in the conventional human diploid normal cell strains mentioned above.

TABLE I

| Cell strain (passage No.) | Susceptibility (PFU/vial) |
| --- | --- |
| LBHEL (+16) | 3625 |
| MRC-5 (+8) | 325 |
| HEL299 (+10) | 300 |
| Lul8 (+8) | 375 |

The LBHEL cell strain of the present invention can be used as a host cell in producing various viruses such as measles, rubella, hepatitis A and varicella vaccine.

A cell-free VZV may be produced by using the LBHEL cell strain of the present invention as follows:
(1) Cell Culture The LBHEL cell strain of the present invention may be cultured in a DME medium(Gibco BRL, U.S.A., Cat. No. 12800-082) containing 5 to 10%(v/v) FBS at a temperature ranging from 36 to 37° C. under an atmosphere of 5% $CO_2$ to form a monolayer.

The split ratio of cells in the monolayer culture may range from 1:5 to 1:10. The cell culture is preferably carried out until 70 to 80% of the surface of the culture vessel is covered with the cells and the cultured cells are then subjected to serial subcultures.
(2) Propagation of VZV VZV may be inoculated to the cultured LBHEL cell strain prepared as above in a multiplicity of infection(MOI) ranging from 1:15 to 1:20. 1 to 1.5 hours after the inoculation, the infected cells may be cultured in a DME medium containing 2 to 5% FBS at a temperature ranging from 36 to 37° C. under an atmosphere of 5% $CO_2$ for 40 to 48 hours. The infected cells may be harvested when the cytopathic effect observed under a microscope (100×) reaches 50% or less, preferably, 30 to 45%. Specifically, the cell culture is washed with a phosphate buffer (pH 7.2) and treated with 0.01 to 0.03% EDTA. The resultant is cultured for 5 minutes and then centrifuged to harvest the VZV-infected cells.
(3) Disruption of Cells and Isolation of Cell-free VZV The VZV-infected cells harvested as above may be disrupted by any conventional method such as ultrasonication and glass beads. Then, cellular debris may be removed by any conventional method such as centrifugation and filtration to provide a supernatant containing cell-free VZV.

The viability of VZV is nearly nil when it is out of its host cell because of its cell-dependent property. Accordingly, the virus is easily inactivated when the virus infected host cell is disrupted. Aforementioned U.S. Pat. No. 4,000,256 describes an attempt to protect VZV during the cell disruption step by adding approximately 7.5 wt % of sucrose in the phosphate buffer. When the virus infected cells are disrupted by ultrasonic wave, virus itself is often crushed and inactivated, thereby reducing the yield of cell-free virus. However, the use of sucrose cushion can not prevent such crush and inactivation of the virus.

The reduction in the yield of the cell-free virus during ultrasonication can be effectively prevented by mixing uninfected LBHEL cells with the infected cells prior to the ultrasonication step. In practicing the present invention, uninfected LBHEL cells are mixed with infected LBHEL cells in the ratio of 1:4 to 3:2.

However, the above method often generates a large amount of cellular debris, thereby causing some loss of the cell-free virus during the purification step such as filtration and centrifugation. In order to solve this problem, the present invention employs a sucrose solution during the purification step such as centrifugation. The sucrose concentration may be 15 wt % or more, preferably, from 15 to 45 wt %.

The above-obtained VZV can be used in preparing vaccines by conventional methods such as attenuation of virus or addition of viral antigens.

The present invention is further described and illustrated in Examples and Test Examples, which are, however, not intended to limit the scope of the present invention.

Commercially available VZV, Varicella Biken Oka virus (ATCC VR-795, Lot no. 6w) was used in the Examples. Hereinbefore and hereinafter, the MRC-5, HEL299 and Lu18 subcultures as provided from ATCC are numbered as passage number 1.

The terms and abbreviations used herein have their normal meaning unless otherwise designated, for example: "°C." refers to degrees Celsius; "M" refers to molar; "v/v" means volume per volume; and "w/v" refers to weight per volume.

EXAMPLE 1

Preparation of LBHEL cell strain

A small portion of human embryonic lung tissue was taken from a 20-week old female embryo having a karyotype of FIG. 1. The tissue was cut into small pieces(2 mm×2 mm) and washed three times with a phosphate buffer(pH 7.2). The resulting tissue pieces were cultured at 36° C. for 5 minutes in a phosphate buffer(pH 7.2) containing 130 units/ml of collagenase and 1 mg/ml of dispase("enzyme solution"). The culture was centrifuged at 200×g for 2 minutes to precipitate the lung tissue. The tissue was collected and cultured in the above enzyme solution at 37° C. for 30 minutes. The culture was centrifuged at 50×g for 2 minutes and the supernatant was neutralized by adding 5% fetal bovine serum(FBS). This enzyme treatment was repeated 4 times until only connective tissues remained.

The combined supernatant was neutralized with 5% FBS, allowed to stand at 4° C. for 1 hour to precipitate the cell aggregates and the supernatant containing single cells was centrifuged at 1000 rpm for 2 minutes. The precipitated cells were collected, dispersed in a DME medium(Gibco BRL, U.S.A., Cat. No. 12800-082) containing 10% FBS to a concentration of $3\times10^5$ cells/ml, and then cultured in a T-flask at 37° C. until the surface of the flask became covered with cells. After treating with a 0.25% trypsin solution, the cells were subjected to serial subcultures.

EXAMPLE 2

Production of VZV virus in LBHEL cell strain (Step 1) Cell Culture

The LBHEL cell strain prepared in Example 1 was cultured in a DME medium(Gibco BRL, U.S.A., Cat. No. 12800-082) containing 5% FBS at 37° C. under an atmosphere of 5% $CO_2$ to form a monolayer. The split ratio of cells in the monolayer culture was adjusted to 1:4. The culture was carried out until 85–95% of the surface -of the culture vessel was covered and the cultured cells were subjected to serial subcultures.

(Step 2) Propagation of VZV

Varicella Biken Oka virus(ATCC VR-795 lot No. 6W) was inoculated to the cultured LBHEL cell strain in a MOI of 1:20. The viral activity was 100,000 to 200,000 plaque forming cell(PFC)/T80 flask (2 ml). The VZV-infected cells were cultured at 37° C. under an atmosphere of 5% $CO_2$. When the cytopathic effect observed under a microscope reached 25 to 45%, the culture was washed three times with a phosphate buffer(pH 7.2) and then treated with 0.02% EDTA. The resultant was cultured for 5 minutes and infected cells were collected and centrifuged at 1000 rpm for about 3 minutes to harvest the infected cells.

(Step 3) Disruption of Cells

The infected LBHEL cells were suspended in an SPGE disruption solution(pH 7.2, 7.5%(w/v) sucrose, 0.0038M potassium phosphate(monobasic), 0.0072M potassium phosphate(dibasic), 0.0049M sodium glutamate, 0.2% EDTA) to a concentration of $5–10\times10^6$ cells/1 ml. The cells were disrupted with microtip(T80 flask) or horn(multitray unit, CF-10) by employing an ultrasonicator (Sonifier, Branson 450) in an ice bath until no protoplasm remained.

(Step 4) Isolation of Cell-free VZV

The resultant was centrifuged at 1000 rpm for 10 minutes to obtain a supernatant containing VZV.

TEST EXAMPLE 1

Normality of the LBHEL cell strain

1) Chromosome Abnormality Test

The LBHEL cell strain prepared in Example 1 was subjected to chromosome abnormality tests including chromosome multiploid test, diploid test,. shape abnormality test, chromosome cleavage test and karyotype analysis test. All tests were conducted by using MRC-5 cell strain as a negative control in accordance with "Biological formulation standard and test method therefor (1992)" published by Department of Public Health of Korea. FIGS. 1—1 and 1–2 show the karyotype of the LBHEL cell strain of the present invention.

2) Tumorigenesis Test

About $2\times10^6$ cells of each of the LBHEL cell strain prepared in Example 1 and Hela cell strain provided from ATCC were subcutaneously injected to 5 or more nude mice deficient in cellular immunity. After 28 days from the injection, no tumor was observed in LBHEL injected mice, whereas tumors have developed in all mice which received Hela cell strain injection.

These experimental results confirm that the human embryonic lung fibroblast LBHEL cell strain of the present invention is a normal diploid cell.

TEST EXAMPLE 2

Comparison of Growth Curves of Cell strains

The growth curve of the LBHEL cell strain of the present invention(KCTC 0127BP) was prepared by measuring the number of cells versus the growth time as follows and then compared with those of MRC-5(ATCC CCL 171) and HEL299(ATCC CCL 137) cell strains.

Each of the test cell strains was cultured on a T80 flask to form a monolayer in accordance with the procedure of (Step 1) of Example 2. The cells were washed three times with a phosphate buffer(pH 7.2) and treated with 0.25% trypsin. After about 2 minutes, the cells were harvested and centrifuged at 1000 rpm for about 3 minutes.

The precipitated cells were suspended in a DME medium containing 5% FBS for LBHEL and 10% FBS for MRC-5 and HEL299, and then added to T80 flasks in an amount of $2\times10^6$ cells/flask. The cells were cultured at 37° C. under an atmosphere of 5% $CO_2$.

At intervals of 24 hours, the number of cells was measured as follows: first, the culture was washed three times with a phosphate buffer(pH 7.2) solution and treated with 0.25% trypsin. After about 2 minutes, the cells were harvested and centrifuged at 1000 rpm for about 3 minutes. The precipitated cells were suspended in a DME medium and spotted on a hemocytometer(Hausser Scientific). The number of cells was counted with a microscope(100×).

Figure 1A:
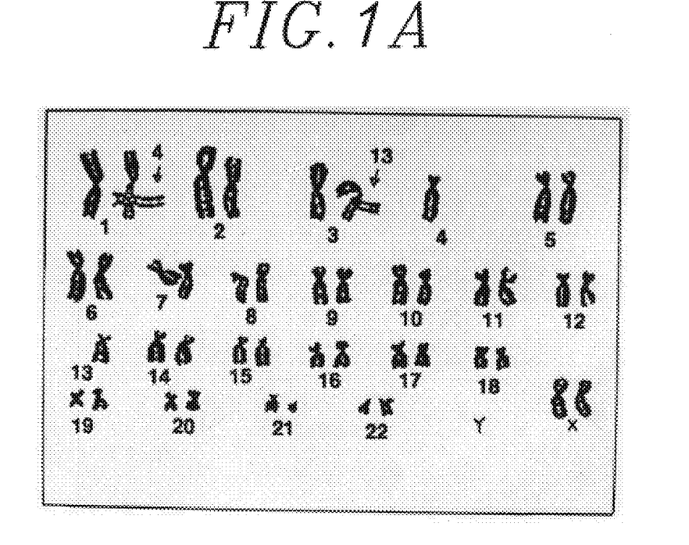
Figure 1B:
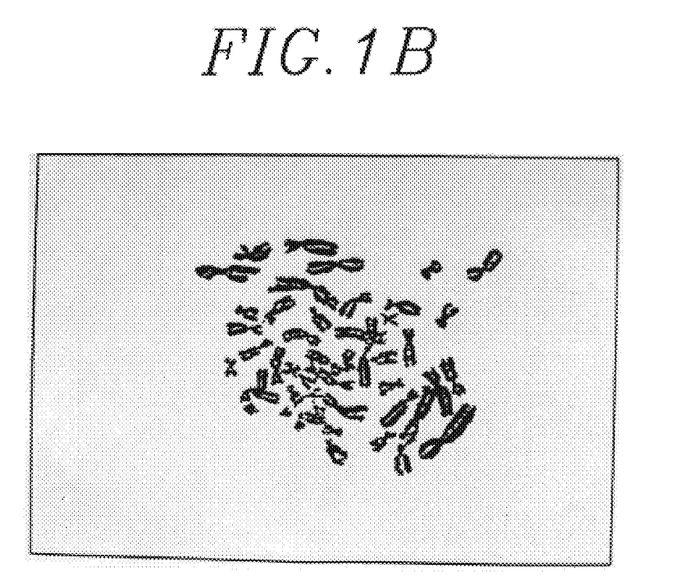
Figure 2:
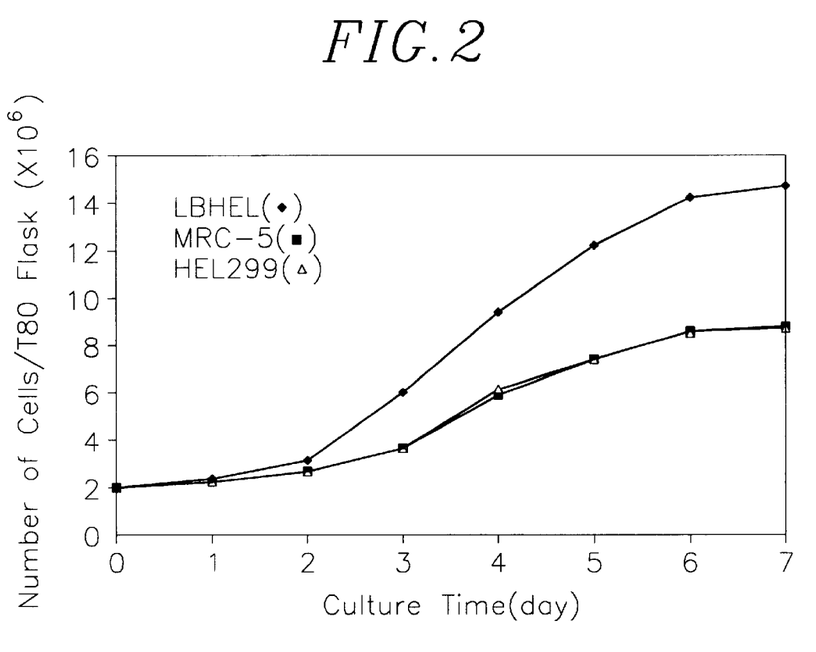
FIG. 2 represents the growth curves of: LBHEL cell strain of the present invention(♦), MRC-5 cell strain (■) and HEL299 cell strain (Δ)

FIG. 2 illustrates the number of cells counted versus the culture time for the LBHEL cell strain of the present invention(♦), MRC-5 cell strain (■) and HEL299 cell strain (Δ). As shown in FIG. 2, LBHEL cell strain exhibits a log phase one day earlier in comparison with MRC-5 and HEL299 cell strains, and the number of LBHEL cell strain was greater than those of the MRC-5 and HEL299 by a factor of about 1.5.

Figure 3:
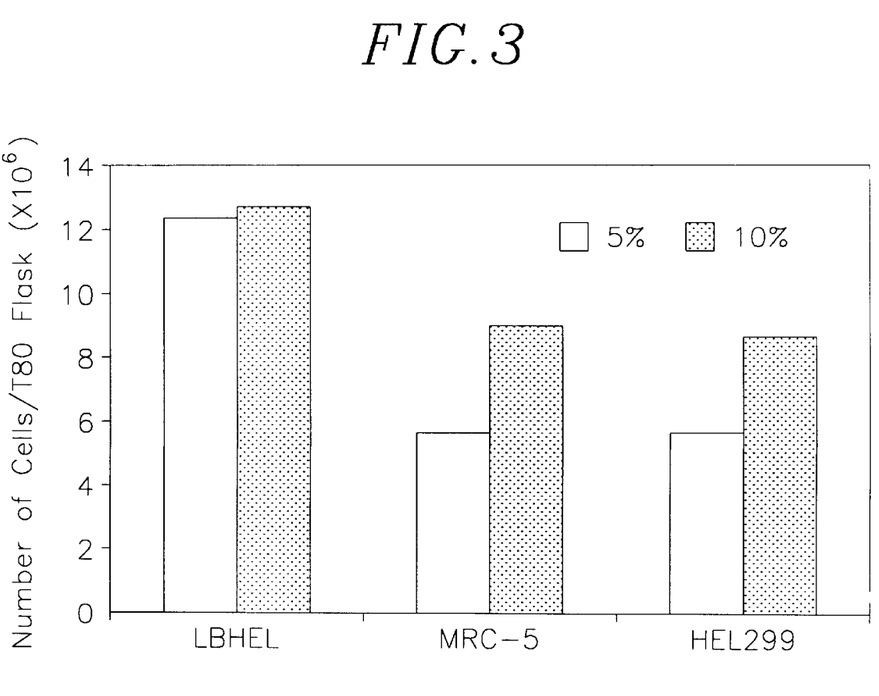
FIG. 3 depicts the number of cells counted after culturing LBHEL cell strain of the present invention, MRC-5 cell strain and HEL299 cell strain in DME medium containing 5% or 10% FBS.

FIG. 3 depicts the number of cells of LBHEL cell strain of the present invention and MRC-5 cell strain and HEL299 cell strain after culturing in a DME medium containing 5% or 10% FBS for 4 days. As shown in FIG. 3, the number of LBHEL cells cultured in a medium containing 5% FBS is nearly the same as that obtained with 10% FBS. In contrast, MRC-5 or HEL299 cell strain does not grow well in a medium containing 5% FBS. This suggests that the LBHEL of the present invention is economically more advantageous than other conventional cell strains.

Further, the LBHEL cell strain of the present invention grew well after 20th subculture. It also grew well in a multitray unit(Nunc 164327, 6000 cm$^2$), which suggests that the LBHEL cell strain can be used in large scale production of virus.

TEST EXAMPLE 3

Susceptibility to VZV

Each of the cell strains shown in Table II was cultured on a Petri dish having a diameter of 60 mm to form a monolayer, in accordance with the procedure of (Step 1) of Example 2, and the cultured cells were washed three times with a phosphate buffer(pH 7.2).

Varicella Biken Oka virus was diluted serially with a DME medium containing 3% FBS. The diluted vaccine was inoculated to the cells in an amount of 0.1 ml/dish. A DME medium containing 3% FBS was added thereto and the resultant was cultured at 37° C. under an atmosphere of 5% $CO_2$ for 7 days.

The number of plaques thus formed was counted with a microscope(40×) and the PFU was calculated to evaluate each cell strain's susceptibility to the virus. The results are shown in Table II.

TABLE II

| Cell strains (Passage No.) | PFU/vial |
| --- | --- |
| LBHEL (+16) | 3625 |
| LBHEL (+20) | 3000 |
| LBHEL (+24) | 2625 |
| MRC-5 (+8) | 325 |
| MRC-5 (+10) | 350 |
| MRC-5 (+12) | 125 |
| HEL299 (+8) | 325 |
| HEL299 (+10) | 300 |
| HEL299 (+12) | 125 |
| Lul8 (+8) | 375 |
| Lul8 (+10) | 325 |
| Lul8 (+12) | 350 |

As shown in Table II, LBHEL cell strain has greater susceptibility than those of MRC-5, HEL299 and Lul8 cell strains by a factor of about 10. Therefore, the LBHEL cell strain of the present invention is useful in the production of VZV vaccine.

TEST EXAMPLE 4

Propagation of VZV in the cell strains.
(Step 1): Inoculation of VZV and Harvest of the Infected Cells Each of the cell strains shown in Table III was cultured in a T80 flask to form a monolayer, in accordance with the procedure of (Step 1) of Examples 2, and the cultured cells were washed three times with a phosphate buffer(pH 7.2).

Varicella Biken Oka virus-infected MRC-5 cell was inoculated to the cells at a viral activity of 100,000 to 200,000 PFC/flask(2 ml).

After 1 hour, a DME medium containing 3% FBS was added thereto and the resultant was cultured at 37° C. under an atmosphere of 5% $CO_2$ for about 48 hours. When the cytopathic effect reached 25 to 45%, the culture was washed three times with a phosphate buffer(pH 7.2) and then treated with 0.02% EDTA. The resultant was cultured for 5 minutes and infected cells were collected and centrifuged at 1000 rpm for about 3 minutes to harvest the infected cells.
(Step 2): Isolation of the Virus The infected cells obtained above were added to SPGE disruption solution(pH 7.2, 7.5%(w/v) sucrose, 0.0038M potassium phosphate(monobasic), 0.0072M potassium phosphate(dibasic), 0.0049M sodium glutamate, 0.2% EDTA) to a concentration of 5–10×10$^6$ cells/1 ml.

The cells were disrupted with an ultrasonicator (Sonifier, Branson 450) by employing a microtip for T80 flask or a horn for multitray unit(CF-10) in an ice bath until no intact cell remained. The resultant was centrifuged at 4° C. and 1000 rpm for 10 minutes to obtain a supernatant containing the virus.
(Step 3) Activity of the Virus LBHEL cell strain was cultured in a Petri dish having a diameter of 60 mm to form a monolayer in accordance with the procedure of (Step 1) of Example 2, and the cultured cells were washed three times with a phosphate buffer(pH 7.2). The infected cells harvested in (Step 1) was added to the monolayer cultured cells in an amount of 0.3 ml/dish for determining the activity of infected cells. Further, the supernatant containing the virus obtained in (Step 2) was diluted sequentially with a 4-fold volume of DME medium and added to the monolayer cultured cells in an amount of 0.1 ml/dish for determining the activity of cell-free virus. The virus was allowed to adsorb to the cells by maintaining the culture at 37° C. under an atmosphere of 5% $CO_2$ for 60 minutes. Then, a DME medium containing 3% FBS was added thereto and the culture was continued under the same conditions as above.

After 6 days, the number of plaques formed was counted with a microscope(40×) and PFC and PFU were calculated therefrom for determining the activities of infected cells and cell-free virus, respectively. The results are shown in Table III.

TABLE III

| Cell strains (Passage No.) | PFC/T80 flask | PFU/T80 flask |
| --- | --- | --- |
| LBHEL (+16) | 2,900,000 | 345,000 |
| LBHEL (+22) | 2,800,000 | 412,500 |
| LBHEL (+26) | 2,600,000 | 180,000 |

TABLE III-continued

| Cell strains (Passage No.) | PFC/T80 flask | PFU/T80 flask |
|---|---|---|
| MRC-5 (+8) | 1,910,000 | 105,000 |
| MRC-5 (+11) | 250,000 | 60,000 |
| MRC-5 (+14) | 1,300,000 | 7,500 |
| HEL299 (+8) | 1,960,000 | 122,500 |
| HEL299 (+11) | 1,725,000 | 127,500 |
| HEL299 (+14) | 1,375,000 | 120,000 |
| Lul8 (+8) | 1,635,000 | 120,000 |
| Lul8 (+12) | 1,265,000 | 62,500 |

As shown in Table III, the activity of VZV in LBHEL of the present invention was higher than those in other conventional cell strains. Specifically, the PFCs of other conventional cell strains are about 50% of that of LBHEL cell, while the PFUs of them reached at most 30% of that of LBHEL cell.

TEST EXAMPLE 5

Effect of Multiplicity of Infection(MOI)

In accordance with the procedure of (Step 1) of Test Example 4, a monolayer culture of LBHEL host cells was prepared and inoculated with Varicella Biken Oka virus-infected MRC-5 cell in a MOI of 1:10, 1:15, 1:20, 1:25 and 1:50, respectively. The PFU values were measured in accordance with the procedures of (Steps 2 and 3) of Test Example 4.

Figure 4:
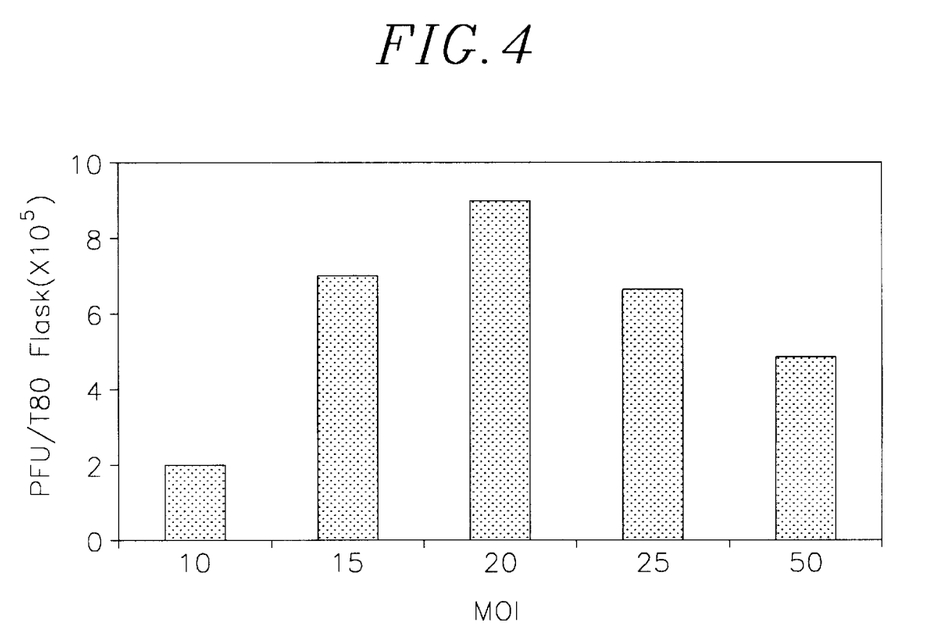
FIG. 4 presents the change in the plaque forming unit (PFU) of the cell-free VZV in LBHEL cell strain of the present invention with multiplicity of infection.

FIG. 4 presents the change in the activity of the cell-free VZV(PFU) in LBHEL cell strain of the present invention with MOI. As shown in FIG. 4, the yield of cell-free virus was highest when MOI is 1:20.

TEST EXAMPLE 6

Effect of Cytopathic Effect on PFU

In accordance with the procedure of (Step 1) of Test Example 4, a monolayer culture of LBHEL cells was prepared and inoculated with Varicella Biken Oka virus-infected MRC-5 cell in a MOI of 1:20. The infected cells were harvested when the cytopathic effect was 12.5, 25, 37.5, 50, 62.5, 75 and 87.5%. The harvested cells were disrupted by ultrasonication and the PFU values were measured in accordance with the procedures of (Steps 2 and 3) of Test Example 4.

Figure 5:
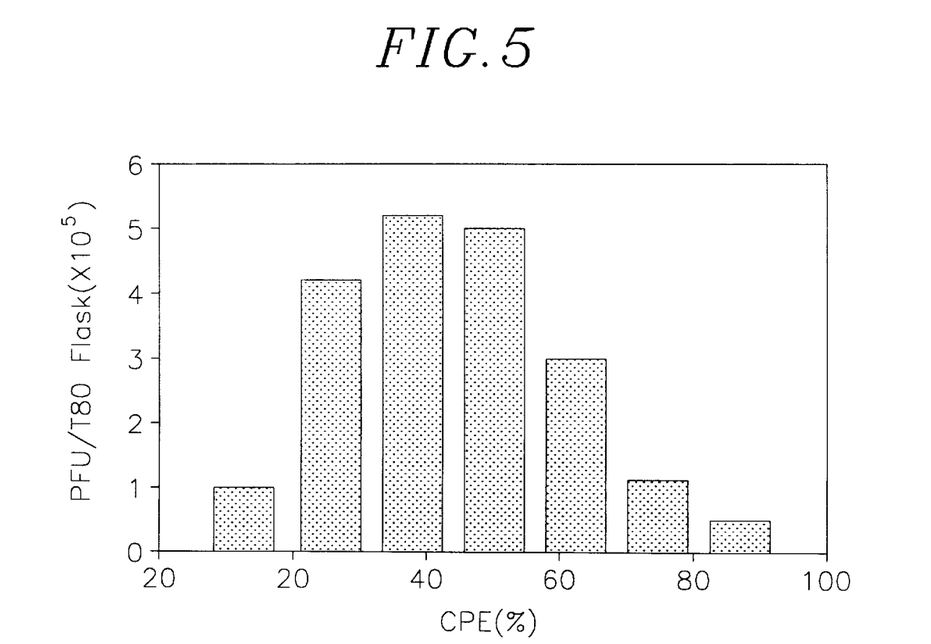
FIG. 5 shows the dependency of the PFU of the cell-free VZV in LBHEL cell strain of the present invention on cytopathic effect.

FIG. 5 shows the activity of the cell-free VZV(PFU) in LBHEL cell strain of the present invention in various cytopathic effects. The yield of the cell-free virus was high when the cytopathic effect is below 50%.

TEST EXAMPLE 7

Stabilization Effect of uninfected cells

The VZV-infected LBHEL cells were prepared in accordance with the procedure of (Step 1) of Test Example 4, and uninfected LBHEL cells were added to the infected LBHEL cells in amounts of 0%, 20%, 40%, 60% and 80% based on the total number of LBHEL cells. The mixture was subjected to an ultrasonication and PFU values were measured in accordance with the procedures of (Steps 2 and 3) of Test Example 4.

Figure 6:
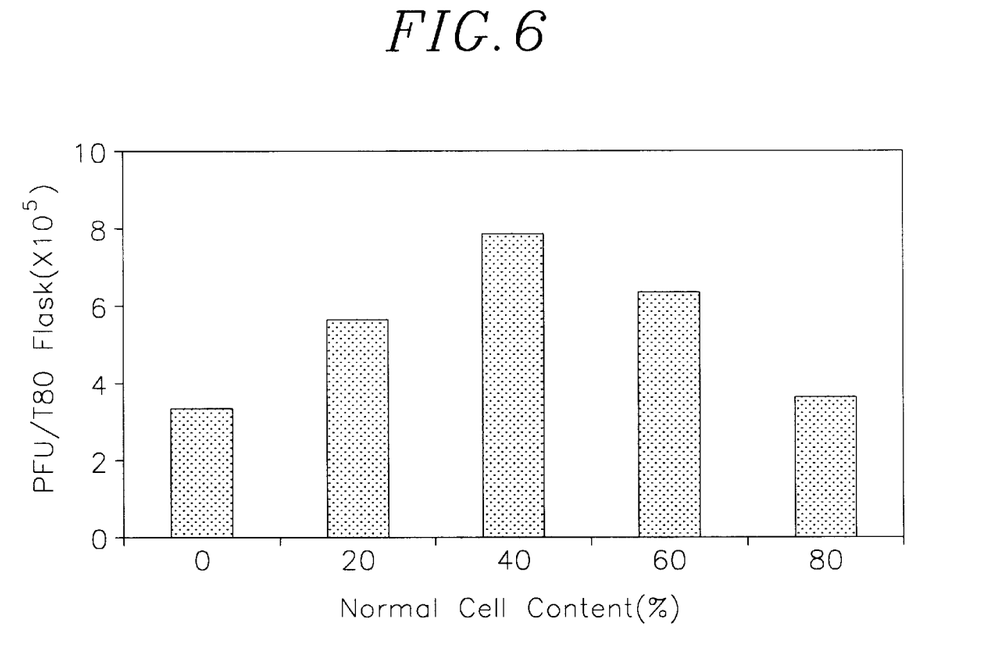
FIG. 6 demonstrates the variation of the PFU of the cell-free VZV as a function of the uninfected LBHEL cell strain content.

FIG. 6 presents the variation of the activity of the cell-free VZV(PFU) as a function of the uninfected LBHEL cell content. As shown in FIG. 6, the activity of the cell-free virus increases when the uninfected cells are present and it becomes highest at an uninfected cell content of 20 to 60% based on the total number of LBHEL cells.

Further, the effect of mixing uninfected cells was evaluated using a multitray unit(CF-10) and the result is shown in Table IV.

TABLE IV

| Infected Cell (%) | Uninfected Cell (%) | PFU/CF10 |
|---|---|---|
| 100 | 0 | 36,270,000 |
| 80 | 20 | 45,330,000 |
| 60 | 40 | 49,130,000 |
| 40 | 60 | 21,500,000 |
| 20 | 80 | 8,310,000 |

As shown in Table IV, uninfected cells can be effectively used to stabilize cell-free VZV in a large scale production of the virus.

TEST EXAMPLE 8

Effect of Sucrose

Infected LBHEL cells were prepared and disrupted by ultrasonication in accordance with the (Steps 1 and 2) of

TEST EXAMPLE 4.

The resultant was centrifuged at 1000 rpm for 10 minutes in the absence or presence of a sucrose solution(pH 7.2, 15–37.5%(w/v) sucrose, 0.0038M potassium phosphate (monobasic), 0.0072M potassium phosphate(dibasic), 0.0049M sodium glutamate, 0.2% EDTA)as shown in Table V and the supernatant containing virus was collected. Then, PFU values were measured in accordance with the procedure of (Step 3) of Test Example 4. The results are shown in Table V.

TABLE V

| Sample | Sucrose % (w/v) | Volume of Sucrose (ml) | PFU |
|---|---|---|---|
| T80 flask | — | — | 441,250 |
| T80 flask | 15 | 1 | 483,750 |
| T80 flask | 22.5 | 1 | 491,340 |
| T80 flask | 30 | 1 | 509,120 |
| T80 flask | 37.5 | 1 | 512,500 |
| CF 10 | — | — | 37,320,000 |
| CF 10 | 15 | 80 | 39,860,000 |

As shown in Table V, the addition of sucrose solution in a concentration ranging from 15 to 37.5%(w/v) stabilizes the VZV.

TEST EXAMPLE 9

Effect of Cell Saturation on the Surface of the Culture Vessel

The LBHEL cell strain of the present invention was cultured in a T80 flask in accordance with (Step 1) of Example 2 to form a monolayer covering 50, 75 or 100% of the total surface area of the culture vessel. The VZV-infected Varicella Oka strain was inoculated to the cells and cultured at 37° C. under an atmosphere of 5% $CO_2$ for 48 hours. Then, PFU values were measured in accordance with the procedures of (Steps 2 and 3) of Test Example 4.

Figure 7:
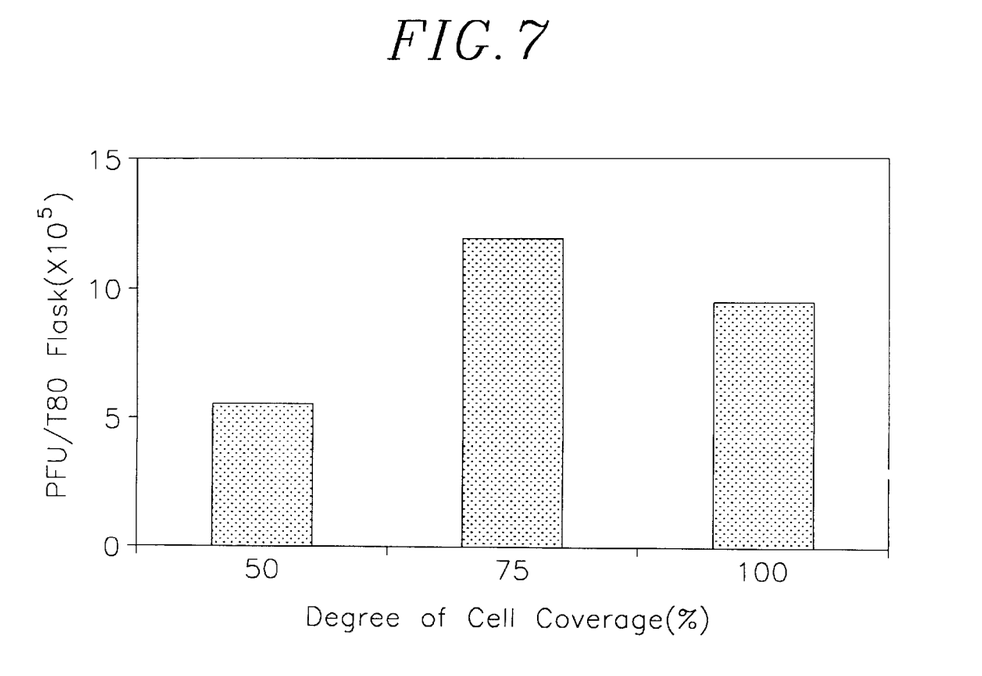
FIG. 7 illustrates how the PFU of the cell-free VZV changes with the degree of cell coverage of the surface of the cell culture vessel.

FIG. 7 shows the change in the activity of the cell-free VZV(PFU) with the degree of cell saturation on the surface of cell culture vessel, wherein the LBHEL cell strain of the present invention exhibits higher susceptibility to VZV at 75% monolayer coverage than at 100% monolayer coverage.

The above results show that the LBHEL cell strain of the present invention is useful in producing various virus vaccines for chickenpox, measles, rubella, mumps, epidemic hemorrhagic fever, Japanese B encephalitis, infantile poliomyelitis, hepatitis A, hepatitis B, hepatitis C and variola.

While the embodiments of the subject invention have been described and illustrated, it is obvious that various changes and modifications can be made therein without departing from the spirit of the present invention which should be limited only by the scope of the appended claims.

What is claimed is:

1. A biologically pure culture of a human embryonic lung fibroblast diploid cell strain having all of the identifying characteristics of a cell strain LBHEL KCTC 0127BP.

2. A process for producing a cell-free varicella zoster virus comprising the steps of:
   (a) culturing a human embryonic lung fibroblast diploid cell strain LBHEL KCTC 0127BP in a culture vessel to give cultured LBHEL cells;
   (b) infecting the cultured LBHEL cells with VZV to give varicella zoster virus infected cells;
   (c) culturing and harvesting the varicella zoster virus infected cells;
   (d) disrupting the harvested cells to obtain a cell homogenate; and
   (e) centrifuging the cell homogenate to obtain a supernatant containing the cell-free varicella zoster virus.

3. The process of claim 2, wherein the LBHEL cell strain is cultured to form a monolayer in step (a) by using a Dulbecco's modified Eagle's medium containing 3 to 10% (v/v) fetal bovine serum.

4. The process of claim 3, wherein the cultured LBHEL cells cover 70 to 80% of the surface of the culture vessel in the monolayer culture of step (a).

5. The process of claim 3 further comprising a step of subjecting the cultured LBHEL cells obtained in step (a) to a subculture in a split ratio ranging from 1:5 to 1:10 when 70 to 80% of the surface of the culture vessel becomes covered with the cultured LBHEL cells.

6. The process of claim 2, wherein the cultured LBHEL cells are harvested in step (c) at a cytopathic effect of 50% or less.

7. The process of claim 6, wherein the cultured LBHEL cells are harvested when the cytopathic effect ranges from 30 to 45%.

8. The process of claim 2 further comprising a step of adding uninfected LBHEL cells to the varicella zoster virus infected LBHEL cells harvested in step (c) before step (d).

9. The process of claim 8, wherein the uninfected LBHEL cells are added in an amount ranging from 20 to 60% based on the total number of the LBHEL cells.

10. The process of claim 2 further comprising a step of adding a sucrose solution having a concentration of 15% (w/v) or more to the cell homogenate obtained in step (d) before step (e).

11. The process of claim 10, wherein the concentration of the sucrose solution ranges from 15 to 45%(w/v).

* * * * *